US009418442B2

(12) United States Patent
Reiter et al.

(10) Patent No.: US 9,418,442 B2
(45) Date of Patent: Aug. 16, 2016

(54) TOOL TRACKING DURING SURGICAL PROCEDURES

(75) Inventors: Austin Reiter, Great Neck, NY (US); Peter K. Allen, Pleasantville, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 146 days.

(21) Appl. No.: 14/234,056

(22) PCT Filed: Jul. 19, 2012

(86) PCT No.: PCT/US2012/047320
§ 371 (c)(1),
(2), (4) Date: Jul. 16, 2014

(87) PCT Pub. No.: WO2013/016113
PCT Pub. Date: Jan. 31, 2013

(65) Prior Publication Data
US 2014/0341424 A1    Nov. 20, 2014

Related U.S. Application Data

(60) Provisional application No. 61/510,797, filed on Jul. 22, 2011.

(51) Int. Cl.
*G06T 7/00* (2006.01)
*G06T 7/20* (2006.01)

(52) U.S. Cl.
CPC ............... *G06T 7/2033* (2013.01); *A61B 34/20* (2016.02); *G06T 7/0042* (2013.01); *G06T 7/0087* (2013.01); *A61B 2034/2065* (2016.02); *G06T 2207/20076* (2013.01)

(58) Field of Classification Search
USPC ........................................................ 382/103
See application file for complete search history.

(56) References Cited

U.S. PATENT DOCUMENTS

2004/0002642 A1* 1/2004 Dekel ................. G06K 9/3216
600/407
2006/0258938 A1 11/2006 Hoffman et al.
(Continued)

FOREIGN PATENT DOCUMENTS

WO    WO-2013016113 A1    1/2013

OTHER PUBLICATIONS

Pezzementi, Zachary, Voros, Sandrine, Hager, Gregory. "Articulated Object Tracking by Rendering Consistent Appearance Parts." 2009 IEEE Conference on Robotics and Automation.*

(Continued)

*Primary Examiner* — Kim Vu
*Assistant Examiner* — Molly Delaney
(74) *Attorney, Agent, or Firm* — Schwegman, Lundberg & Woessner, P.A.

(57) ABSTRACT

A system and method for tracking a surgical implement in a patient can have an imaging system configured to obtain sequential images of the patient, and an image recognition system coupled to the imaging system and configured to identify the surgical implement in individual images. The image recognition system can be configured to identify the surgical implement relative to the patient in one of the images based, at least in part, on an identification of the surgical implement in at least one preceding one of the sequential images, and a probabilistic analysis of individual sections of the one of the images, the sections being selected by the image recognition system based on a position of the surgical implement in the patient as identified in the at least one preceding one of the images.

24 Claims, 4 Drawing Sheets

(56) References Cited

U.S. PATENT DOCUMENTS

| | | | |
|---|---|---|---|
| 2009/0088897 A1* | 4/2009 | Zhao | G06K 9/3216 |
| | | | 700/250 |
| 2010/0121181 A1* | 5/2010 | Wang | A61B 6/12 |
| | | | 600/424 |
| 2010/0331855 A1 | 12/2010 | Zhao et al. | |
| 2012/0188351 A1* | 7/2012 | Kaku | G06T 7/0016 |
| | | | 348/65 |

OTHER PUBLICATIONS

"European Application Serial No. 12817697.1, Extended European Search Report mailed Nov. 26, 2014", 4 pgs.

Allenn, Brian, et al., "Visual Tracking of Laparoscopic Instruments in Standard Training Environments", (Feb. 2011), 7 pgs.

Giannarou, S., et al., "Affine-invariant anisotropic detector for soft tissue tracking in minimally invasive surgery", IEEE International Symposium on Biomedical Imaging: From Nano to Macro, 2009. ISBI '09., (2009), 1059-1062.

Hu, Tie, et al., "Insertable Stereoscopic 3D Surgical Imaging Device with Pan and Tilt", Proceedings of the 2nd Biennial IEEE/RAS-EMBS International Conference on Biomedical Robotics and Biomechatronics, (Oct. 19-22, 2008), 311-316.

Hu, Tie, et al., "Insertable Surgical Imaging Device with Pan, Tilt, Zoom, and Lighting", 2008 IEEE International Conference on Robotics and Automation, (May 19-23, 2008), 2948-2953.

Mountney, Peter, et al., "Soft Tissue Tracking for Minimally Invasive Surgery: Learning Local Deformation Online", Medical Image Computing and Computer-Assisted Intervention—MICCAI 2008: Lecture Notes in Computer Science, vol. 5242, (2008), 364-372.

Reiter, Austin, et al., "An Online Learning Approach to In-Vivo Tracking Using Synergistic Features", The 2010 IEEE/RSJ International Conference on Intelligent Robotics and Systems, (Oct. 18-22, 2010), 3441-3446.

Sánchez-González, P., et al., "Laparoscopic video analysis for training and image-guided surgery", Minim Invasive Ther Allied Technol., 20(6), (Dec. 2011), 311-20.

Xu, Kai, et al., "System Design of an Insertable Robotic Effector Platform for Single Port Access (SPA) Surgery", The 2009 IEEE/RSJ International Conference on Intelligent Robots and Systems, (Oct. 11-15, 2009), 5546-5552.

"European Application Serial No. 12817697.1, Office Action mailed Mar. 12, 2014", 3 pgs.

"European Application Serial No. 12817697.1, Response filed Jun. 6, 2014 to Office Action mailed Mar. 12, 2014", 12 pgs.

"International Application Serial No. PCT/US2012/047320, Search Report mailed Oct. 5, 2012", 2 pgs.

"International Application Serial No. PCT/US2012/047320, Written Opinion mailed Oct. 5, 2012", 8 pgs.

"International Application Serial No. PCT/US2012/047320, International Preliminary Report on Patentability mailed Feb. 6, 2014", 10 pgs.

* cited by examiner

TOOL TRACKING DURING SURGICAL PROCEDURES

STATEMENT REGARDING FEDERALLY SPONSORED RESEARCH DEVELOPMENT

This invention was made with government support under award number 5R21EB007779-02 from the National Institute of Health.

The government has certain rights in this invention.

CLAIM OF PRIORITY

This application is a U.S. National Stage Application filed under 35 U.S.C. 371 of International Application Serial No. PCT/US2012/047320, filed on Jul. 19, 2012, which application claims the benefit of priority of U.S. Provisional Patent Application No. 65/510,797, entitled "AN ADAPTIVE SURGICAL TOOL TRACKING ALGORITHM FOR USE DURING SURGICAL PROCEDURES," which was filed on 22 Jul. 2011, which applications are incorporated herein by reference in their entirety.

TECHNICAL FIELD

This document pertains generally to the tracking of surgical implements, and more particularly, but not by way of limitation, to visual tracking of surgical implements using adaptive algorithms and related methods.

BACKGROUND

Various technologies have been utilized to track the position of surgical implements in a patient. Ultrasound and other indirect imaging techniques can display a representation of the surgical implement on a screen. Fiduciary markers that show up on ultrasound images, for instance, have been positioned at known locations on or within the patient. The position of the surgical implement can then be compared against the positions of the fiduciary markers to give an approximated position of the surgical implement relative to the markers.

OVERVIEW

This document describes a system to track a surgical implement during a surgical procedure. While contemporary surgical implement tracking can usefully provide position information for the surgical implement, the use of fiduciary markers can create a variety of challenges. The fiduciary markers necessarily have to be placed in useful locations on or in the patient, which can require costly operating room time and, potentially, separate or lengthened surgical procedures to place the fiduciary markers in the locations. The fiduciary markers can be more limited in scope than potential anatomical features of the patient; a patient can have far more anatomical features than it can be realistic to associate with fiduciary markers. Consequently, certain anatomical features can create obstacles to moving and positioning a surgical implement that are not necessarily made apparent by the fiduciary markers.

Visual systems can be utilized to guide surgical implements during surgical procedures. A medical professional could, for instance, position a camera to show the environment around a surgical implement. However, the simple use of a camera could require or encourage constant attention by the medical professional, reducing a potential utility of automated or robotic surgical procedures. In addition, because of changing conditions in a patient, such as changing light levels at different locations in the patient's body, recognition of tools and anatomical features can be made challenging to medical professionals and image recognition systems over time.

Further, because conventional image recognition systems can rely on known views and aspects of previously initialized objects, surgical conditions can create difficulties for such conventional image recognition systems. Because surgical implements can often be twisted and manipulated during surgical procedures, the image recognition system can be presented with aspects of the surgical implement for which the image recognition system has not been initialized and might not recognize. In addition, because surgical procedures can utilize multiple, occasionally unusual surgical implements on short notice, the image recognition system can encounter surgical implements that have not been initialized and that are otherwise unknown to the image recognition system.

The surgical implement tracking system and related methods described herein can utilize a probabilistic analysis of a visual image to identify the surgical implement. The system can identify the surgical implement in individual ones of a series of images. The probabilistic analysis of one of the series of images can be based on the identification of the surgical implement in a preceding one of the series of images. The probabilistic analysis can incorporate separate analysis of a variety of image characteristics, such as image color, texture, edge identification, corner identification, curvature, size, orientation, object area, and so forth. As a result, surgical implements can be identified in a variety of aspects and in a variety of visual conditions.

Example 1 can include subject matter that can include a device-assisted method for tracking a surgical implement previously introduced into a patient. The method can include obtaining sequential images of the patient, using a processor circuit, probabilistically analyzing individual sections of one of the images to generate a probabilistic analysis, the individual sections selected using information about a previous position of the surgical implement as identified in at least one preceding one of the images, and, using the processor circuit, identifying the surgical implement in individual images at least in part using the probabilistic analysis and information about an identification of the surgical implement in at least one preceding one of the images.

In Example 2, the subject matter of Example 1 can optionally include that probabilistically analyzing the sections is based on probabilistically analyzing image characteristics of the sections.

In Example 3, the subject matter of any one or more of Examples 1 and 2 can optionally include that the sequential images are visual images, and that the image characteristics include at least one of color, texture, an edge of an object, a corner of the object, curvature, size of the object, orientation of the object, and area of the object.

In Example 4, the subject matter of any one or more of Examples 1-3 can optionally include that probabilistically analyzing the individual sections comprises, for individual image characteristics, determining a likelihood that the individual image characteristic corresponds to the surgical implement, and determining a likelihood that the individual section corresponds to the surgical implement based on the likelihoods of the individual image characteristics.

In Example 5, the subject matter of any one or more of Examples 1-4 can optionally include that the likelihood that the individual section corresponds to the surgical implement is based on a weighted average of the likelihoods of the individual image characteristics.

In Example 6, the subject matter of any one or more of Examples 1-5 can optionally include that the weighted average is a dynamically weighted average based on the likelihood of the individual image characteristics relative to a standard likelihood.

In Example 7, the subject matter of any one or more of Examples 1-6 can optionally include that the sections are equally sized, the sections comprise a search region, and a size of the search region of one of the images is selected at least in part using a number of immediately preceding images in which the surgical implement was not identified.

In Example 8, the subject matter of any one or more of Examples 1-7 can optionally include the individual sections are one pixel in size.

In Example 9, the subject matter of any one or more of Examples 1-8 can optionally include that the search region for one of the images is sized equal to a number of search pixels adjacent to a pixel in which the surgical implement has been identified.

In Example 10, the subject matter of any one or more of Examples 1-9 can optionally include storing, in a database, at least one physical feature of the surgical implement as identified in at least one of the images, and wherein the surgical implement is identified using the physical feature of the surgical implement as stored in the database.

In Example 11, the subject matter of any one or more of Examples 1-10 can optionally include that the at least one physical feature comprises different physical features of the surgical implement identified in at least one of the images, and wherein a physical feature of the surgical implement is added to the database upon being identified in one of the images.

In Example 12 the subject matter of any one or more of Examples 1-11 can optionally include storing the at least one physical feature in the database comprises storing the sequential images in the database at specified intervals.

In Example 13, the subject matter of any one or more of Examples 1-12 can optionally include storing the at least one physical feature in the database comprises storing a current image based on a change in an aspect of the at least one physical feature relative to a preceding image stored in the database.

In Example 14 the subject matter of any one or more of Examples 1-13 can optionally include that the sequential images are captured by a camera configured to capture aspects of the surgical implement in the images, and wherein identifying the surgical implement is based at least in part on the aspects.

In Example 15, the subject matter of any one or more of Examples 1-14 can optionally include that the sequential images are captured by cameras situated in a specified interrelationship, and identifying the surgical implement identifies a three-dimensional position of the surgical implement.

In Example 16, the subject matter of any one or more of Examples 1-15 can optionally include displaying, on a user interface, a track of the position of the surgical implement in the patient, as identified by the image recognition system.

In Example 17, the subject matter of any one or more of Examples 1-16 can optionally include obtaining, using the user interface, a user input that identifies the surgical implement in a first one of the images.

Example 18 can include subject matter that can include a system for tracking a surgical implement in a patient. The system can comprise an imaging system configured to obtain sequential images of the patient and an image recognition system coupled to the imaging system and configured to identify the surgical implement in individual images. The image recognition system is configured to identify the surgical implement relative to the patient in one of the images based, at least in part, on an identification of the surgical implement in at least one preceding one of the sequential images and a probabilistic analysis of individual sections of the one of the images, the sections being selected by the image recognition system based on a position of the surgical implement in the patient as identified in the at least one preceding one of the images.

In Example 19, the subject matter of Example 18 can optionally include that the probabilistic analysis is based on a probabilistic analysis of image characteristics of the sections.

In Example 20, the subject matter of any one or more of Examples 18 and 19 can optionally include that the sequential images are visual images, and wherein the image characteristics include at least one of color, texture, an edge of an object, a corner of the object, curvature, size of the object, orientation of the object, and area of the object.

In Example 21, the subject matter of any one or more of Examples 18-20 can optionally include that the probabilistic analysis of the individual sections is based, at least in part, on for individual image characteristics, a likelihood that the individual image characteristic corresponds to the surgical implement, and a likelihood that the individual section corresponds to the surgical implement based on the likelihoods of the individual image characteristics.

In Example 22, the subject matter of any one or more of Examples 18-21 can optionally include that the likelihood that the individual section corresponds to the surgical implement is based on a weighted average of the likelihoods of the individual image characteristics.

In Example 23, the subject matter of any one or more of Examples 18-22 can optionally include that the weighted average is a dynamically weighted average based on the likelihood of the individual image characteristics relative to a standard likelihood.

In Example 24, the subject matter of any one or more of Examples 18-23 can optionally include that the sections are equally sized, the sections comprise a search region, and a size of the search region of one of the images is selected at least in part using a number of immediately preceding images in which the surgical implement was not identified.

In Example 25, the subject matter of any one or more of Examples 18-24 can optionally include that the individual sections are one pixel in size.

In Example 26, the subject matter of any one or more of Examples 18-25 can optionally include that the search region for one of the images is sized equal to a number of search pixels adjacent to a pixel in which the surgical implement has been identified.

In Example 27, the subject matter of any one or more of Examples 18-26 can optionally include a database configured to store at least one physical feature of the surgical implement as identified in at least one of the images, and wherein the surgical implement is identified using the physical feature of the surgical implement as stored in the database.

In Example 28, the subject matter of any one or more of Examples 18-27 can optionally include that the at least one physical feature comprises different physical features of the surgical implement identified in at least one of the images, and wherein a physical feature of the surgical implement is added to the database upon being identified in one of the images.

In Example 29, the subject matter of any one or more of Examples 18-28 can optionally include that the database is configured to store the at least one physical feature in the database by storing the sequential images in the database at specified intervals.

In Example 30, the subject matter of any one or more of Examples 18-29 can optionally include that the database is configured to store the at least one physical feature in the database based on a current image based on a change in an aspect of the at least one physical feature relative to a preceding image stored in the database.

In Example 31 the subject matter of any one or more of Examples 18-30 can optionally include that the imaging system comprises a camera configured to capture aspects of the surgical implement in the images, and wherein the surgical implement is identified based at least in part on the aspects.

In Example 32, the subject matter of any one or more of Examples 18-31 can optionally include that the imaging system comprises cameras situated in a specified interrelationship, and the image recognition system is configured to identify a three-dimensional position of the surgical implement.

In Example 33, the subject matter of any one or more of Examples 18-21 can optionally include a user interface configured to display a track of the position of the surgical implement in the patient, as identified by the image recognition system.

In Example 34, the subject matter of any one or more of Examples 18-21 can optionally include that the user interface is configured to obtain a user input that identifies the surgical implement in a first one of the images.

Example 35 can include subject matter that can include a storage medium comprising instructions that, when executed on a processor, cause the processor to obtain sequential images of the patient, probabilistically analyze individual sections of one of the images to generate a probabilistic analysis, the individual sections selected using information about a previous position of the surgical implement as identified in at least one preceding one of the images, and identify the surgical implement in individual images at least in part using the probabilistic analysis and information about an identification of the surgical implement in at least one preceding one of the images.

In Example 36, the subject matter of Example 35 can optionally include probabilistically analyzing the sections is based on probabilistically analyzing image characteristics of the sections.

In Example 37, the subject matter of any one or more of Examples 35 and 36 can optionally include that the sequential images are visual images, and wherein the image characteristics include at least one of color, texture, an edge of an object, a corner of the object, curvature, size of the object, orientation of the object, and area of the object.

In Example 38, the subject matter of any one or more of Examples 35-37 can optionally include that probabilistically analyzing the individual sections is based on instructions to cause the processor to, for individual image characteristics, determine a likelihood that the individual image characteristic corresponds to the surgical implement, and determine a likelihood that the individual section corresponds to the surgical implement based on the likelihoods of the individual image characteristics.

In Example 39, the subject matter of any one or more of Examples 35-38 can optionally include that the likelihood that the individual section corresponds to the surgical implement is based on a weighted average of the likelihoods of the individual image characteristics.

In Example 40, the subject matter of any one or more of Examples 35-39 can optionally include that the weighted average is a dynamically weighted average based on the likelihood of the individual image characteristics relative to a standard likelihood.

In Example 41, the subject matter of any one or more of Examples 35-40 can optionally include that the sections are equally sized, the sections comprise a search region, and a size of the search region of one of the images is selected at least in part using a number of immediately preceding images in which the surgical implement was not identified.

In Example 42, the subject matter of any one or more of Examples 35-41 can optionally include that the individual sections are one pixel in size.

In Example 43, the subject matter of any one or more of Examples 35-42 can optionally include that the search region for one of the images is sized equal to a number of search pixels adjacent to a pixel in which the surgical implement has been identified.

In Example 44, the subject matter of any one or more of Examples 35-43 can optionally include that the instructions cause the processor to store, in a database, at least one physical feature of the surgical implement as identified in at least one of the images, and wherein the surgical implement is identified using the physical feature of the surgical implement as stored in the database.

In Example 45, the subject matter of any one or more of Examples 35-44 can optionally include that the at least one physical feature comprises different physical features of the surgical implement identified in at least one of the images, and wherein a physical feature of the surgical implement is added to the database upon being identified in one of the images.

In Example 46, the subject matter of any one or more of Examples 35-45 can optionally include that the instructions that cause the processor to store the at least one physical feature in the database cause the processor to store the sequential images in the database at specified intervals.

In Example 47, the subject matter of any one or more of Examples 35-46 can optionally include that the instructions that cause the processor to store the at least one physical feature in the database cause the processor to store a current image based on a change in an aspect of the at least one physical feature relative to a preceding image stored in the database.

In Example 48, the subject matter of any one or more of Examples 35-47 can optionally include that the instructions that cause the processor to capture the sequential images are captured by a camera configured to capture aspects of the surgical implement in the images, and wherein the instructions that cause the processor to identify the surgical implement are based at least in part on the aspects.

In Example 49, the subject matter of any one or more of Examples 35-48 can optionally include that the sequential images are captured by cameras situated n a specified interrelationship, and wherein the instructions cause the processor to identify a three-dimensional position of the surgical implement.

In Example 50, the subject matter of any one or more of Examples 35-49 can optionally include instructions that cause the processor to display, on a user interface, a track of the position of the surgical implement in the patient as identified.

In Example 51, the subject matter of any one or more of Examples 35-50 can optionally include instructions that cause the processor to obtain, using the user interface, a user input that identifies the surgical implement in a first one of the images.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

System Overview

Figure 1:
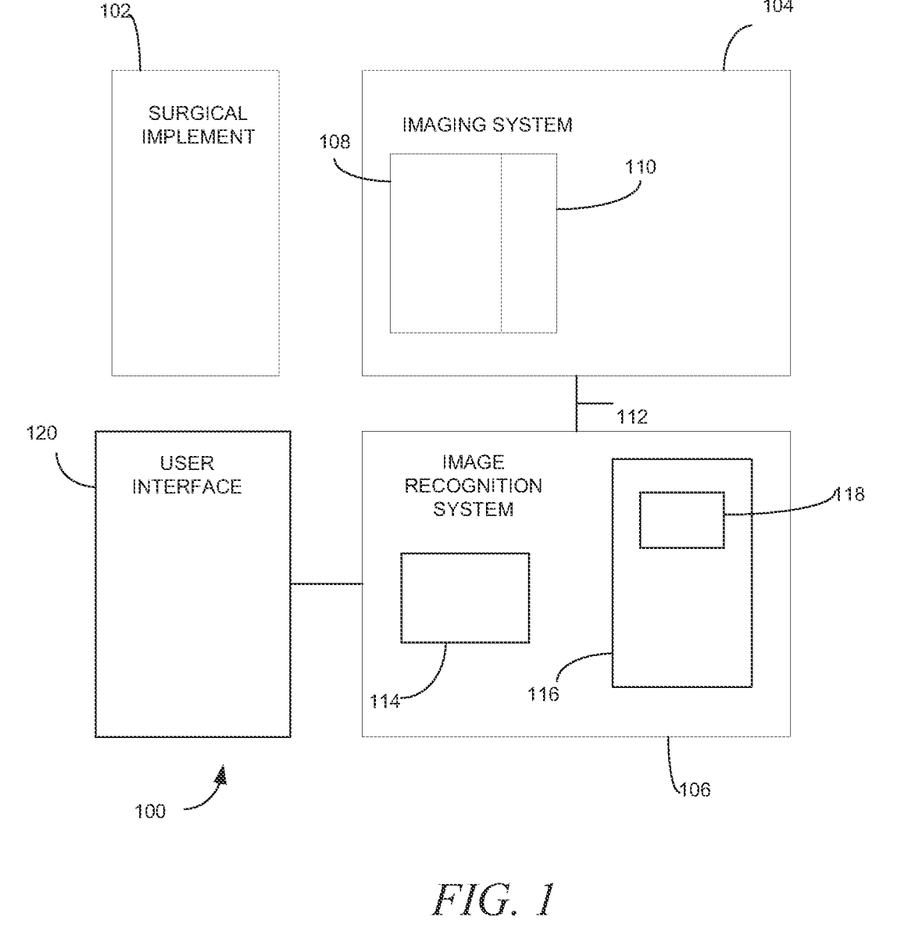
FIG. 1 shows a block diagram of a system for tracking a surgical implement in a patient.

FIG. 1 shows a block diagram of a system 100 for tracking a surgical implement 102 in a patient. The system 100 includes an imaging system 104 and an image recognition system 106. The imaging system 104 can include an imaging device 108, such as a camera. The camera can be configured to detect light in the spectrum visible to the human eye, and certain cameras can be sensitive to light outside of the visible spectrum. The camera can be configured to detect color rather than only grayscale. The imaging device 108 can incorporate multiple cameras, for instance two cameras, such as can provide stereoscopic imaging. The imaging device 108 can be or include a computed tomography (CT) scanner, a magnetic resonance imaging (MRI) scanner, X-ray or other medical or non-medical scanner or image generation system. The imaging device 108 can present images in real time, which can be understood as providing the images substantially immediately upon acquiring the images. The imaging device 108 can obtain or record discrete images and/or video. It is to be understood that video can include multiple discrete images obtained sequentially and rapidly, and thus video can be deconstructed into multiple sequential images that can be separately and independently analyzed for content.

The imaging system 104 can include a support structure 110. The imaging device 108 can be mounted on or with respect to the support structure 110. The support structure 110 can be utilized to position the imaging device 108 with respect to the surgical implement 102 and a patient. The imaging device 108 can be articulable or rotatable with respect to the support structure 110 to allow the imaging device 108 to change a focal point without necessarily having to reposition the support structure 110.

The imaging system 104 can be biocompatible, such as to support insertion into a patient during a surgical procedure. The imaging system 104 can further include various electronic devices that can support the generation and saving of visual images in a digital format, such as can be generated when the imaging device 108 is a digital camera, as known in the art. For example, the imaging system 104 generally, or the imaging device 108 specifically, can include a processor and electronic data storage such as a hard disk or standard computer or electronic device memory like random access memory (RAM) or flash or other electrically erasable and programmable read only memory (EEPROM). The processor can support generation of digital images while the electronic data storage can store the digital images at least until the digital images are transmitted to the image recognition system 106. The electronic data storage can be configured to store at least one and, in certain examples, multiple images.

The image recognition system 106 can be communicatively coupled to the imaging system 104 via a communication link 112. The communication link 112 can utilize wired communication or wireless communication technologies according to standard or proprietary modalities as well known in the art. Where the communication link 112 is wireless, the imaging system 104 can be sterilized for use in a sterile filed while the image recognition system 106 can be positioned outside of the sterile field. Where the communication link 112 is wired, or in certain instances where the communication link 112 is wireless, various components of the system 100 can be positioned in various relationships to a sterile field.

The image recognition system 106 can include a processor 114 and electronic data storage 116 such as a hard disk or standard computer or electronic device memory. The electronic data storage 116 can include a database 118 for storing visual images as transmitted from the imaging system 104. The database 118 can include multiple sequential visual images that can be utilized in the analysis of a current image and/or subsequent images. Alternatively, the electronic data storage 116 can store the sequential images without respect to organizing the images in a database 118 or other organized structure.

The processor 111 can be configured to analyze individual ones of the images as transmitted by the imaging system 104 to identify and track the surgical implement 102 with respect to the patient and the patient's anatomy. It is to be understood that while the image recognition system 106 is described here with respect specifically to identifying and/or tracking surgical implements 102, the principles applicable to identifying the surgical implement 102 can be applied equally well to other objects in other circumstances. The system 100 generally, and the image recognition system 106 specifically, can be applied to identify and track various objects in various environments for or of which images can be obtained.

The system 100 can optionally include a user interface 120. The user interface 120 can be configured to display images from the imaging system 104 for inspection by a user, such as on a display as well known in the art. The user interface 120 can be further configured to receive a user input, such as on the a touchscreen associated with the display or via a keyboard or other electronic input device. The user input can, for instance, initialize a particular object, such as to provide a basis for subsequent analysis by the image recognition system 106, as discussed below.

Imaging System

Figure 2:
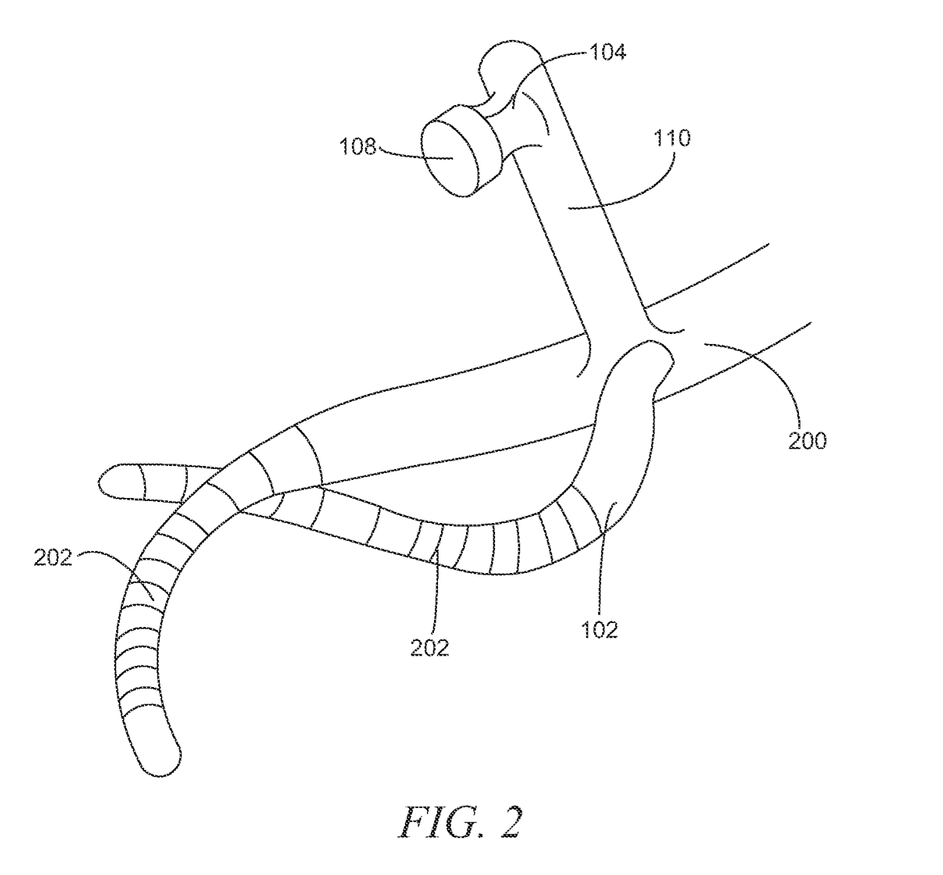
FIG. 2 is a drawing of an exemplary imaging system positioned with respect to a surgical implement.

FIG. 2 is a drawing of an exemplary imaging system 104 positioned with respect to an exemplary surgical implement 102. The surgical implement 102 as presented is merely presented for non-limiting illustrative purposes, and the imaging system 104 can be utilized with any suitable surgical implement 102 or, as noted above, any object in general. The imaging system 104 includes an exemplary imaging device 108 mounted with respect to the support structure 110. The support structure 110 is positioned with respect to the surgical implement 102, as illustrated by being attached to a shaft 200 of the surgical implement 102. Manipulation and positioning of the surgical implement 102 thereby positions, at least in part, the imaging system 104.

The surgical implement 102, as illustrated, includes articulable and extendable arms 202. The imaging device 108 can be positioned to provide visual images of one or more of the arms 202 with respect to the environment in which the arm 202 is positioned. The imaging device 108 can rotate and actuate with respect to the support structure 110 so as to keep at least one arm 202 within a visual field of the imaging device 108. The imaging device 108 can include two lenses, for instance to generate stereoscopic images. The communication link 112 can transmit the stereoscopic images to the image recognition system 106.

The surgical implement 102 can be a component of a robot or can be robot-controlled. In an example, the image recognition system 106 can be communicatively coupled to a control mechanism of the surgical implement 102. Based on an output of the image recognition system 106, the control mechanism of the image recognition system 106 can maneuver the arms 202 and the surgical implement 102 generally. For instance, the arms 202 can be positioned at a location so that surgical tools positioned on or with respect to the arms 202 can perform surgical activities. Such surgical tools could include blades, drills, electrodes, and so forth. The maneuvering of the arms 202, for instance, can be so as to avoid anatomical features of the patient that might obstruct access of the arms 202 to a target location.

Flowcharts for Recognizing the Surgical Implement

Figure 3:
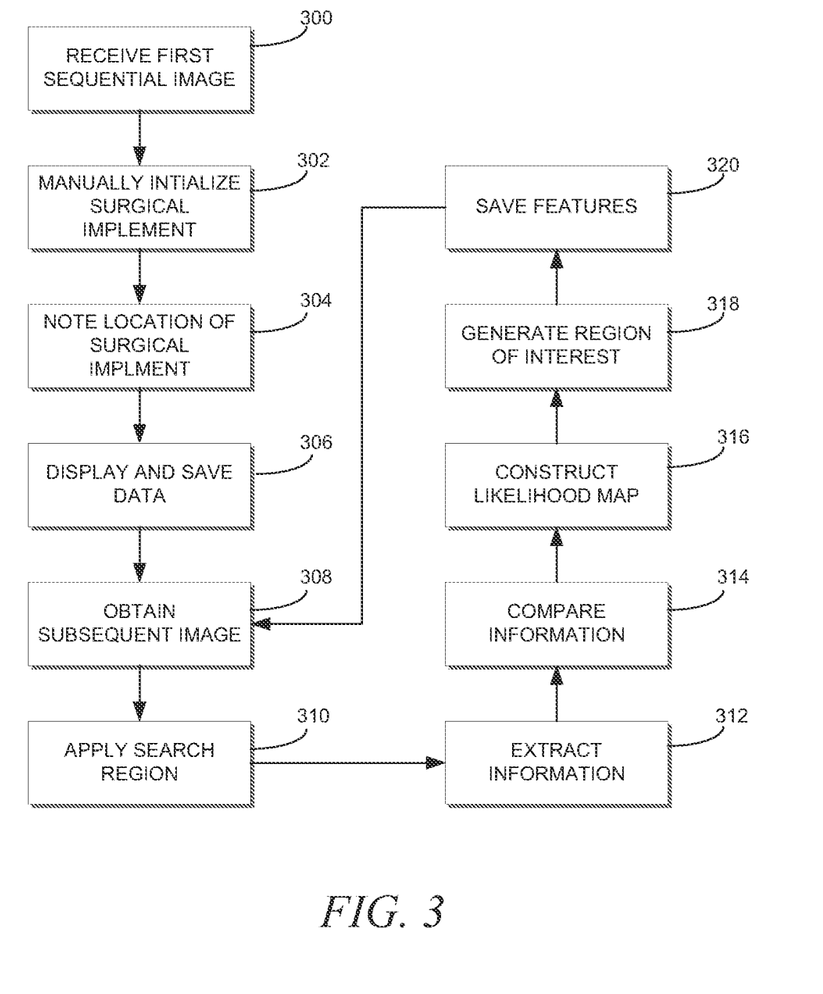
FIG. 3 is a flowchart for recognizing a surgical implement using an image recognition system.

FIG. 3 is a flowchart for recognizing the surgical implement 102 using the image recognition system 106. The image recognition system 106 can utilize a probabilistic analysis as detailed below to recognize the surgical implement 102. The flowchart can operate as the imaging system 104 obtains and transmits multiple sequential visual images to the image recognition system 106. As discussed above, the multiple sequential visual images can be digital images obtained through discrete frames or images or through a video feed. The visual images can be transmitted to the image recognition system 106, and the various blocks of the flowchart discussed below can be implemented as images are received from the image recognition system 106.

At 300, a first one of the sequential visual images is received by the image recognition system 106.

At 302, a user can utilize the user interface 120 to manually initialize the surgical implement 102 in the first one of the images. In such an example, the user interface 120 can include a display and a touchscreen or other input device, such as a mouse or trackball. The user can initialize the surgical implement 102 by physically selecting the surgical implement, such as by touching the surgical implement 102 on the touchscreen or marking the surgical implement 102 with a cursor controlled by the mouse or trackball.

At 304, the system 100 generally, and the image recognition system 106, processor 114, and user interface 120 specifically, can note a location of the user selection and denote an object in the location as the surgical implement 102. The object can be identified in the location based on a nature of one or more sections of the image at or near the location of the user selection. One section can be one pixel in size. Based on the pixel or pixels at the selected location, the image recognition can utilize the color of the pixels, the texture of the object implied by the pixels, identification of edges as implied by the pixels, identification of corners as implied by the pixels, and other image recognition techniques known in the art. Pixels of the image that correspond generally to at least one of the color, texture, edges, and corners of the location selected by the user can be identified by the image recognition system 106 as showing the surgical implement 102.

At 306, at least one of the first image and the data related to the surgical implement 102 as displayed on the first image can be saved in the database 118. As identified at 304, the data relating to the surgical implement 102 can include a raw list of the identity of the pixels of the image that correspond to the surgical implement 102. The data relating to the surgical implement 102 can include relative positions of pixels that correspond to the surgical implement 102 with respect to one another; stated another way, the data relating to the surgical implement 102 can detail a shape of the surgical implement 102. Instead of or in addition to being stored in the database 118, the first image or the data relating to the surgical implement 102 can be stored in relatively shorter-term memory of the data storage 116, such as in RAM, to make the image or data available relatively quickly for subsequent analysis.

The database 118, potentially in combination with the data storage 116, can maintain track states of the surgical implement 102. The track state maintained in the database 118 can be a representative sample of the surgical implement 102, such as samples of different aspects of the surgical implement 102 obtained from various images. Each track state can include: the image corresponding to the aspect of the surgical implement 102; a search region or region of interest of the image corresponding to the surgical implement 102 and surrounding parts of the image, as discussed in detail below; and image characteristics of the surgical implement 102 in the image, such as color, texture, edges, and corners. The surgical implement 102 as initialized by the user in the first image can provide a first one of the track states of the surgical implement 102.

At 308, the imaging system 104 can obtain a subsequent sequential image. The subsequent sequential image can be can be obtained with the imaging system 104 positioned in the same location as a preceding sequential image or with the imaging system 104 having been repositioned relative to the preceding image.

At 310, the image recognition system 106 can apply a search region to the subsequent, now "current" image. The image recognition system 106 can utilize the track state of the surgical implement 102 as previously identified and stored in the database 118. In particular, the image recognition system 106 can apply a region of interest of one or more preceding track states and images as the search region of the current image. The region of interest as applied to the current image can be the identical region of interest as applied to a preceding image or can be modified, such as by increasing the scope of the region of interest to include pixels immediately adjacent to the pixels of the preceding region of interest. The current region of interest can be based on a region of interest of an immediately preceding image or, if the image recognition system 106 did not identify the surgical implement 102 in the immediately preceding image, of a region of interest of an image that precedes the immediately preceding image. The region of interest can be iteratively expanded by one or more sections, such as one pixel, for every sequential image in which the surgical implement 102 is not identified.

At 312, the image recognition system 106 can extract information from the search region of the current image. For instance, the image recognition system 106 can extract image characteristics, such as color, texture, edges, and corners, from the search region. The extracted information can be stored in the data storage 116.

At 314, the image recognition system 106 can compare the extracted information from the search region of the current image with related information from the track state of preceding images stored, for instance, in the database 118 and/or the data storage 116. The extracted information can be compared between and among related data. For instance, a normalized cross-correlation of sections around identified corners identified from the current image can be compared against other sections around corners of images in which the surgical implement 102 was identified. The sections can be one pixel in size or larger. For instance, an alignment between potential matching features of the surgical implement in the current image and a preceding image can be estimated. Outlying matches can be deleted utilizing an estimation technique to fit a model to observations, such as the m-estimator sample consensus ("M-SAC") or the random sample consensus ("RANSAC") known in the art.

An estimation technique such as M-SAC can select a number of random or pseudo-random points to compute a model. The model can be an equation that, for instance, best fits the selected points. The model as estimated based on the random points can be evaluated against observations, such as sections corresponding to the potential matching features, and an error score of the observations to the model can be computed. The points can be iteratively selected and can be less than the total number of observations. Selections can proceed for a preselected number of iterations or until the error score is less than a preselected minimum. M-SAC utilizing iterative selection of points relative to a preselected minimum error rate can, under certain circumstances, be relatively less susceptible to large outlying observations than utilizing a preselected number of iterations or, for instance, RANSAC.

In further examples, the alignment of the search region of the current image can be compared against warped information from the track state, such as the region of interest from preceding images or the image of the surgical implement 102 as identified in the preceding images. The warped information can account for changes in perspective relating to movement of the surgical implement 102, the imaging system 104, or both. The warped track state information can be based on the alignment as estimated above. Affine arithmetic models known in the art can be utilized for numerical analysis of the warped information from the track state. Based on the analyses conducted by the image recognition system 106, including but not necessarily limited to some of those detailed above, the image recognition system 106 can identify a preceding track state that represents a best match to the search region of the current image.

At 316, the image recognition system 106 can construct a likelihood map of the current image. The likelihood map can define areas of the current image, such as areas of the search region, that are relatively likely to contain the surgical implement 102 relative to areas that are unlikely to contain the surgical implement 102. Likely areas can be assigned with high probability values while unlikely areas can be assigned with low probability values. Relatively likely regions can be identified based on the comparison of the extracted data of the current image with the best match of the track state as identified at 314. The areas that are relatively likely can include sections where the surgical implement 102 was previously identified, and sections, such as individual pixels, that are directly adjacent to sections in which surgical implement 102 was previously identified.

The likelihood map can be based on a variety of probabilities that can be identified in the search region of the current image and the best match of the track state. The probabilities of various image characteristics can be assessed, such as color, texture, and other mathematically-identifiable features of the image. In an example, an overall likelihood that the search region of the current image includes the surgical implement 102 can be defined as:

$$P_i = \sum_k w_k P_k \qquad \text{Equation 1}$$

$P_i$ is the overall probability that the search region of the current image corresponds to the surgical implement 102, $w_k$ is a weight for each image characteristic, $P_k$ is a probability for each characteristic, and k is the number of image characteristics assessed. The weights can sum to "1". The weights can be dynamically weighted for various conditions, with certain image characteristics weighted more strongly relative to a standard likelihood. For instance, in environments where there is relatively substantial amounts of light, color can be weighted relatively strongly. For instance, in environments with relatively weak light, identified curves can be weighted relatively strongly.

Where an image characteristic is color, various "seed" features can incorporate linear combinations of colors in the visual color space to compute local image window histograms. The seed features can then be utilized as known "tuned" colors against which other colors in the current image and the track state can be compared. Various physical features of the search region of the image, such as are identified by edge and corner analysis, can be converted into normalized histograms. The histograms can be normalized according to each element within each physical feature of the surgical implement 102, such as the arms 202, and according to various sections of the physical feature or individual pixels of the physical feature. The normalized histograms can constitute a probability distribution function for each physical feature. Physical features that are relatively prominent, such as those displayed in the foreground of the image, can be assessed separately from physical features that are relatively less prominent, such as those displayed in the background of the image. Relatively less prominent features can be obtained from a larger search region than relatively prominent features. The seed features can be formed from a log-likelihood ratio of the probability distribution function:

$$L(i) = \log \frac{(\max\{p(i) \cdot \delta\})}{(\max\{q(i), \delta\})} \qquad \text{Equation 2}$$

In the probability distribution function, p can be the probability of the surgical implement 102 or other object in the foreground, q can be the probability relating to background objects, and δ can prevent taking a logarithm of zero of dividing by zero. Discrimination between different features of the surgical implement 102 can be based on a two-class variance ratio, with the variance for the surgical implement 102 or other object in the foreground probability p being:

$$\text{var}(L;p) = E[L^2(i)] - (E[L(i)])^2 \qquad \text{Equation 3}$$

The variance for the background probability q can be computed according to Equation 3 by substituting q for references to p. The variance ratio for the log-likelihood function is thus:

$$VR(L; p, q) = \frac{\text{var}\left(L; \frac{p+q}{2}\right)}{\text{var}(L; p) + \text{var}(L; q)} \qquad \text{Equation 4}$$

Color features can be scored based on the variance ratio. The largest variance ratio, which can indicate the most-distinctly discriminated feature in the image, can be chosen as the "tuned" color the subject image.

The tuned color can be identified bused, for instance, on a previous identification of the surgical implement 102. In such a circumstance, a color that is most distinctly associated with the surgical implement 102 can be identified the tuned color corresponding to the surgical implement 102. Such a color can be identified, for instance, by having been associated with the largest variance as determined above, such as in the current image or in a preceding image. Colors that are identified in previous images as being the tuned color can be stored in, for instance, a lookup table in the database 118 or data storage 116. The number of times a particular color is identified in the look up table as a tuned color can serve as a weight for future analysis of various colors.

A color that is identified as having high variance and a high weight can serve as the tuned from which to compare other colors in the subject image. The lookup table can incorporate a color chart that includes known relationships between various colors. Based on the tuned color for an image as identified above, the lookup table can identify an anticipated appearance of other colors given ambient lighting conditions. On the basis of the comparisons of the anticipated appearance of the other colors, pixels throughout the subject image can be assessed for color.

Where an image characteristic is a corner in the image, a Gaussian prior can be performed on an initial estimate of a location of the corner. The initial estimate of the location of the corner can be based on a location of the corner in a preceding one of the images, such as an immediately preceding image. A two-dimensional elliptical Gaussian function as known in the art can be applied to define a region where the corner is expected. The elliptical Gaussian function can be parameterized so that the function is centered at the initial estimated location. The function can be shaped based on dimensions of the corner as previously identified. The dimensions can, for instance, be rectangular based on the corner as previously identified.

In an example, the mean of the Gaussian function is the estimated two-dimensional center of the region of interest. A sub-region or "track patch" of the image can be identified, wherein half of a track patch can be defined as one standard deviation of the Gaussian function. Based on a section's location in a region of interest and relationship to the previously identified corner, a likelihood that that particular section corresponds to the surgical implement 102 can be determined.

Texture can be characterized based on changes in a spatial image gradient within an image. Texture can be re-identifiable between images separated in time and can be locally discriminative, in that texture can be identifiable relative to conditions local to the texture regardless of if the texture is globally identifiable within the image. A corner feature can be a section of the image in which the object is re-localizable and can be used to identify the location of the object in subsequent images.

Where an image characteristic is a texture of an object, the track patch identified with respect to the Gaussian function can be utilized with an affine transformation to identify and preserve straight lines to identify warping in the subject image. The warping can be compensated for in the identification of textures in the subject image. Texturing can further or optionally be identified without compensating for warping. Based on previously identified texture characteristics, the texture of the object corresponding to each section, for instance in the region of interest, can be utilized to determine a likelihood that the section corresponds to the surgical implement 102.

Other image characteristics, including edges, curvature, size, orientation, area, and so forth, can be incorporated in ways known in the art. Based on the identified probabilities for the various computed image characteristics, the function of Equation 1 can be run and the overall likelihood of the surgical implement 102 being in the region of interest identified.

At 318, the image characteristics as identified at 316 can be utilized as seed points in the generation of the region of interest for sequential images. Outlying sections, such as individual pixels, that have abnormally high likelihoods can be eliminated based on probabilistic analyses. For instance, individual sections that vary from surrounding sections by more than one standard deviation, or by a more or less rigorous standard, can be identified as outliers and eliminated from further consideration.

The likelihood of the surgical implement 102 being at the expected location in the region of interest can be based on a number of times in preceding images the surgical implement 102 was identified. Where the surgical implement 102 was identified in a relatively large number of preceding images, the current image can be approached with a relatively high likelihood of finding the surgical implement in a relatively narrow expected region of interest or search region, potentially creating relatively large variances in likelihoods for sections not within the expected region of interest. The less the variance in likelihood between individual sections, the fewer outliers can or may be eliminated from further consideration.

One cause of reduced variance between sections can be a relatively low likelihood that the surgical implement 102 is in any particular location from a previously identified image. As such, if the surgical implement 102 is not identified in a preceding image, then the likelihood of finding the surgical implement 102 in a relatively narrow specific location in the current image can decrease. As a result, various sections at increasing numbers of locations in the image can have likelihoods that are not so significant outliers as to be eliminated from further consideration, resulting in an increase in the search region or region of interest. Hence, the search region may expand, such as by one section, such as one pixel, around each existing section of the previous search region. Once the surgical implement 102 is identified again, the region of interest may reduce by the same process described above.

At 320, particular physical features of the surgical implement 102 can be identified, such as the shaft 200 or the arm 202. Sections of the image that are identified as likely relating to the surgical implement 102 can be correlated to previously identified features of the surgical implement 102 based on the image characteristics. Thus, sections that combine to incorporate likelihoods for colors, textures, and curves, for instance, can have those image characteristics compared against, previously identified image characteristics of the arm 202. Sections that can combine to show a relatively high likelihood of colors, textures, and curves that correspond to the same or similar previously identified colors, textures, and curves of the arm 202 can be identified as the arm 202.

Upon completion of 308-320, subsequent images can be obtained and analyzed iteratively per 308-320 as can be needed or useful to a surgical procedure or other circumstance where image recognition can be useful.

Figure 4:
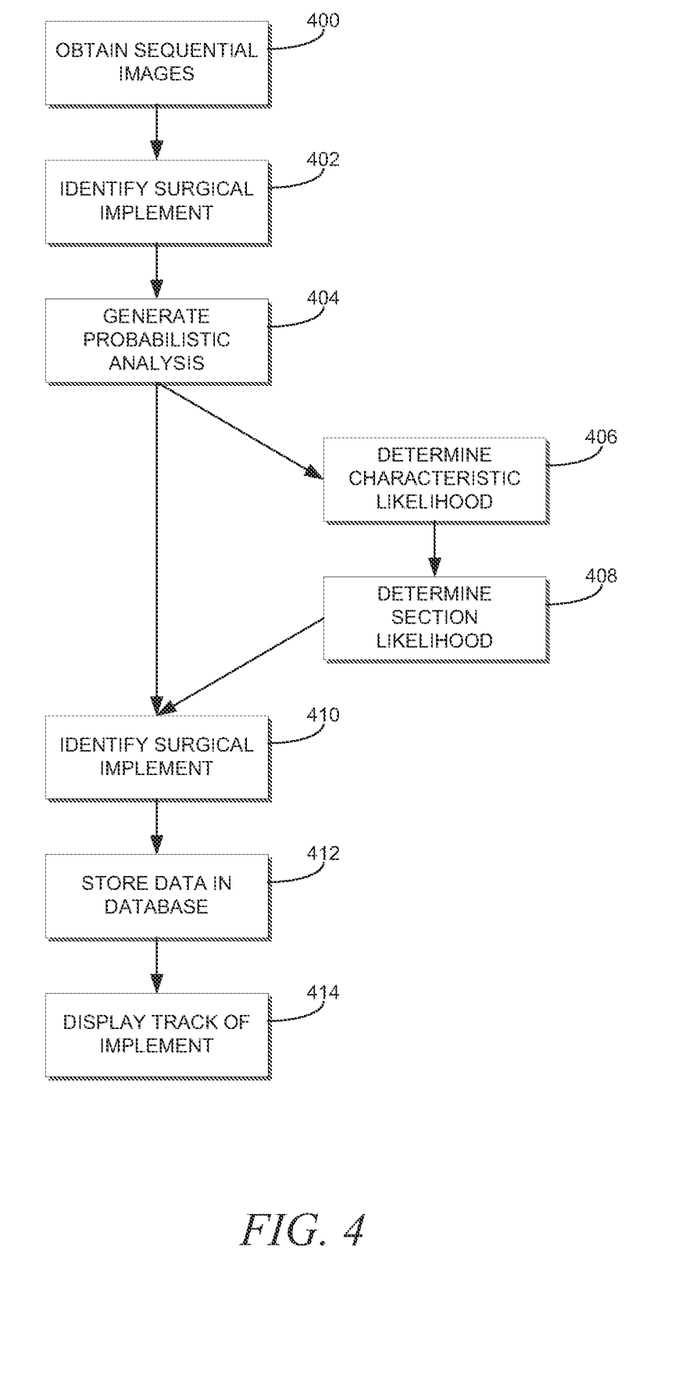
FIG. 4 is a flowchart for tracking a surgical implement previously introduced into a patient.

FIG. 4 is a flowchart for tracking a surgical implement previously introduced into a patient. The surgical implement can be the surgical implement 102 of the system 100. The surgical implement 102 can be tracked with the devices of the system 100, or can be tracked according to other devices and systems that are suitable for doing so. Additionally, while the flowchart is presented with respect to tracking the surgical implement 102 in a patient, the various steps of the flowchart can be implemented with respect to generic objects in generic circumstances and are not limited solely to medical environments.

At 400, sequential images of a patient are obtained. The sequential images can be obtained using the imaging device 108 of the imaging system 104, such as a camera for capturing visual images. The imaging system 104 can include multiple cameras positioned in a specified interrelationship, such as can produce a three-dimensional position of the surgical device 102, as discussed below. The sequential images can be obtained by using an imaging device such as a computed tomography (CT) scanner, a magnetic resonance imaging (MRI) scanner, X-ray or other medical or non-medical scanner or image generation system. The imaging device can capture discrete images or video, and can be presented in real time.

At 402, a user can identify the surgical implement 102 in one of the sequential images. The user can use the user interface 120 to select the surgical implement on a display. The user can identify the surgical implement 102 in a first one of the sequential images.

At 404, individual sections of one of the sequential images can be probabilistically analyzed to generate a probabilistic analysis. Individual sections, such as individual pixels, can be selected from the image based on information about the surgical implement 102 as previously identified. Such information can include image characteristics of the surgical implement as well as position information about the surgical implement 102 in at least a preceding image of the sequential images. The probabilistic analysis of the individual sections can be based on the image characteristics as applied to the individual sections. The image characteristics can include color, texture, an edge of an object, a corner of the object, curvature, size of the object, orientation of the object, and area of the object.

The individual sections can be equally sized. Each section can be one pixel in size. Taken together, the individual sections can make up a search region or region of interest. The size of the search region can be selectable based on a number of immediately preceding images in which the surgical implement was not identified 102. The selection of the number of sections in the search region can be based on relative likelihoods of individual sections. The search region for any one image can be based on sections that correspond to a location of the surgical implement 102 and sections that are immediately adjacent to the sections in which the surgical implement 102 has been identified.

At 406, probabilistically analyzing the image can optionally include determining a likelihood that an individual image characteristic corresponds to the surgical implement 102. For instance, a particular color in the image can be identified as corresponding to a color associated with surgical implement 102.

At 408, probabilistically analyzing the image can optionally include determining a likelihood that a section, such as a pixel, corresponds to the surgical implement 102 based on the image characteristics of the section. The likelihood that the section corresponds to the surgical implement 102 can be based on a weighted average of the likelihoods of the individual characteristics. The weighted average can be a dynamically weighted average.

At 410, the surgical implement 102 can be identified based on the probabilistic analysis and the previous position information of the surgical implement 102. The surgical implement 102 can be identified by a processor circuit 114, such as can be a part of, or operate in conjunction with the image recognition system 106.

At 412, data relating to a physical feature of the surgical implement 102, as identified in the image, is stored in a database, such as in the database 118. For instance, the physical feature can be one of the shaft 200 or the arm 202. The data relating to the physical feature can be stored in the database 118 upon the physical feature being identified. Each physical feature of the surgical implement 102 that is identified can be separately saved in the database.

Different images of same physical feature, such as the arm 202, can be stored in the database 118. For instance, such images can incorporate different aspects of the same physical feature. Images of different aspects of the physical features of the surgical implement 102 can be utilized in identifying the physical feature, specifically, and the surgical implement 102, generally, with the image recognition system 106. Different images of the physical features can be stored at specified intervals, such as regular intervals.

At 414, a track of the surgical implement 102 is displayed on a user interface 120. The tack of the surgical implement 102 can include a current position of the surgical implement 102 and/or a representation of past positions of the surgical implement.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein," Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description can include reference to a microprocessor, a processor circuit, a signal processor, a controller circuit, or the like. Such terms can include, among other things, a microcontroller including one or more of a volatile or non-volatile memory, multiple input/output channels, an analog-to-digital converter, a power supply, a digital-to-analog converter, or one or more other circuits, modules, or components that, in an example, can be co-integrated in a single integrated circuit, a single circuit package, a multi-chip module package, a hybrid, a polyimide flex-circuit assembly, or the like. In some examples, the implementations of such devices can be logically realized as, for example, a microcontroller, programmable logic device (e.g., field programmable gate array), state machine, or the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A device-assisted method for tracking a surgical implement previously introduced into a patient, the method comprising:
    obtaining sequential images of the patient;
    using a processor circuit, probabilistically analyzing individual sections of one of the images to generate a probabilistic analysis, the individual sections selected using information about a previous position of the surgical implement as identified in a multitude of preceding images; and
    using the processor circuit, identifying the surgical implement in individual images at least in part using the probabilistic analysis and at least in part using information about an identification of the surgical implement in a multitude of preceding images,
    wherein said probabilistic analysis is based on a multitude of image characteristics from said multitude of preceding images, said image characteristics corresponding to a physical feature of said surgical implement, said image characteristics being stored in one or more databases, wherein the surgical implement is identified using the multitude of image characteristics as stored in said one or more databases,
    said databases receiving and storing new image characteristics, said new image characteristics being extracted from said sequential images upon being identified, said new image characteristics being further used to identify the surgical implement.

2. The method of claim 1, wherein probabilistically analyzing the sections is based on probabilistically analyzing a multitude of color image characteristics from a multitude of color images of the sections.

3. The method of claim 2, wherein the sequential images are visual images, and wherein the image characteristics include at least one of color, texture, an edge of an object, a corner of the object, curvature, size of the object, orientation of the object, and area of the object.

4. The method of claim 2, wherein probabilistically analyzing the individual sections comprises:
    for individual image characteristics, determining a likelihood that the individual image characteristics corresponds to the surgical implement; and
    determining a likelihood that the individual section corresponds to the surgical implement based on the likelihoods of the individual image characteristics.

5. The method of claim 4, wherein the likelihood that the individual section corresponds to the surgical implement is based on a weighted average of the likelihoods of the individual image characteristics.

6. The method of claim 5, wherein the weighted average is a dynamically weighted average based on the likelihood of the individual image characteristics relative to a standard likelihood.

7. The method of claim 1:
    wherein the sections are equally sized;
    wherein the sections comprise a search region; and
    wherein a size of the search region of one of the images is selected at least in part using a number of immediately preceding images in which the surgical implement was not identified.

8. The method of claim 7 wherein the individual sections are one pixel in size.

9. The method of claim 8 wherein the search region for one of the images is sized equal to a number of search pixels adjacent to a pixel in which the surgical implement has been identified.

10. The method of claim 1, wherein storing the image characteristics in the database comprises storing the sequential images in the database at specified intervals.

11. The method of claim 1, wherein storing the image characteristics in the database comprises storing a current image based on a change in an aspect of at least one physical feature of the surgical implement relative to a preceding image stored in the database.

12. The method of claim 1, wherein the sequential images are captured by a camera configured to capture aspects of the surgical implement in the images, and wherein identifying the surgical implement is based at least in part on the aspects.

13. The method of claim 12, wherein the sequential images are captured by cameras situated in a specified interrelationship, and identifying the surgical implement identifies a three-dimensional position of the surgical implement.

14. The method of claim 1, further comprising displaying, on a user interface, a track of the position of the surgical implement in the patient, as identified by the image recognition system.

15. The method of claim 14, further comprising obtaining, using the user interface, a user input that identifies the surgical implement in a first one of the images.

16. A system for tracking a surgical implement in a patient, comprising:
   an imaging system configured to obtain sequential images of the patient; and
   an image recognition system coupled to the imaging system and configured to identify the surgical implement in individual images;
   wherein the image recognition system is configured to identify the surgical implement relative to the patient in one of the images based, at least in part, on:
   an identification of the surgical implement in at least one preceding one of the sequential images; and
   a probabilistic analysis of a multitude of individual sections of the at least one of the sequential images,
   wherein said probabilistic analysis is based on a multitude of image characteristics from said multitude of individual sections, said image characteristics corresponding to physical features of said surgical implement, said image characteristics being stored in one or more databases, wherein the surgical implement is identified using the multitude of image characteristics as stored in said one or more databases, and
   said databases receiving and storing new image characteristics, said new image characteristics being extracted from said sequential images upon being identified, said new image characteristics being further used to identify the surgical implement.

17. The system of claim 16, wherein the probabilistic analysis is based on a probabilistic analysis of a multitude of color image characteristics from a multitude of color images of the sections.

18. The system of claim 17, wherein the sequential images are visual images, and wherein the image characteristics include at least one of color, texture, an edge of an object, a corner of the object, curvature, size of the object, orientation of the object, and area of the object.

19. The method of claim 1, further comprising an affine transform step to identify the physical characteristics of the surgical implement when said image characteristics change with regard to scale.

20. The method of claim 1, wherein said image characteristics comprise one or more colors.

21. The method of claim 1, wherein said image characteristics comprise textures.

22. The method of claim 1, wherein said image characteristics comprise sizes of an object.

23. The method of claim 1, wherein said image characteristics comprise orientations of an object.

24. The method of claim 1, wherein said image characteristics comprise areas of an object.

* * * * *